United States Patent
Tarr

(10) Patent No.: US 6,577,709 B2
(45) Date of Patent: Jun. 10, 2003

(54) FRACTIONAL MONITOR UNIT RADIATION DELIVERY CONTROL USING DOSE RATE MODULATION

(75) Inventor: Randall V. Tarr, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 41 days.

(21) Appl. No.: 09/850,464

(22) Filed: May 7, 2001

(65) Prior Publication Data

US 2001/0017907 A1 Aug. 30, 2001

Related U.S. Application Data

(63) Continuation of application No. 09/100,457, filed on Jun. 18, 1998.

(51) Int. Cl.[7] .................................................. H05G 1/44

(52) U.S. Cl. ............................. 378/108; 378/65; 378/97

(58) Field of Search ............................. 378/65, 97, 108

(56) References Cited

U.S. PATENT DOCUMENTS

| | | | | |
|---|---|---|---|---|
| 6,108,399 A | * | 8/2000 | Hernandez-Guerra et al. | 378/65 |
| 6,249,565 B1 | * | 6/2001 | Tarr | 378/65 |

* cited by examiner

Primary Examiner—Drew A. Dunn
Assistant Examiner—Jurie Yun

(57) ABSTRACT

Method and system aspects for achieving more accurate radiation delivery during radiation treatment by a radiation-emitting system are described. In a method aspect, and system for achieving same, the method includes providing a table of dose rate values for accumulated dosages in a treatment unit of the radiation emitting system, and controlling a dose rate of radiation emitted from the radiation emitting system through utilization of the table of dose rates. Controlling further includes determining an accumulated dosage at a sampling point, and comparing the accumulated dosage to a total desired dosage. The dose rate is adjusted based on the table of dose rate values and the determined accumulated dosage, with the dose rate ramped down as the accumulated dosage nears the total desired dosage. Accumulated dosages include fractional numbers of monitor units.

8 Claims, 3 Drawing Sheets

1

FRACTIONAL MONITOR UNIT RADIATION DELIVERY CONTROL USING DOSE RATE MODULATION

CROSS REFERENCE TO RELATED APPLICATION

This application is a continuation of patent application Ser. No. 09/100,457, filed Jun. 18, 1998.

FIELD OF THE INVENTION

The present invention relates to radiation-emitting devices, and more particularly, to providing better control of radiation delivery from radiation-emitting devices.

BACKGROUND OF THE INVENTION

Radiation-emitting devices are generally known and used for radiation therapy in the treatment of patients, for example. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. During treatment, the radiation beam is provided on one zone of a patient lying in the isometer of gantry rotation.

The delivery of radiation by a radiation therapy device is normally prescribed and approved by an oncologist with administration by a therapist. Typical therapy involves programming the device by the therapist to deliver the radiation beam at a known and constant rate of a chosen number of monitor units per time period, (e.g., MU/minute), where a monitor unit generically refers to a dose unit of radiation for a chosen calibration. Monitoring of the total dose delivered at a chosen time interval, for example, every 10 milliseconds, determines when the total desired dosage has been provided to end the therapy. Unfortunately, the total dosage may be slightly exceeded, since a sampling point usually does not occur at a precise point of completion of the desired total dosage delivery. Even slight excesses of radiation are considered highly undesirable.

Thus, while typical therapy does provide needed radiation treatment, improvements in the process of delivering a prescribed total dose are still desirable. Accordingly, what is needed is a method and system for providing a desired total dosage with greater control and accuracy, including fractional monitor unit delivery control.

SUMMARY OF THE INVENTION

The present invention provides a method and system for achieving more accurate radiation delivery during radiation treatment by a radiation-emitting system. In a method aspect, and system for achieving same, the method includes providing a table of dose rate values for accumulated dosages in a treatment unit of the radiation emitting system, and controlling a dose rate of radiation emitted from the radiation emitting system through utilization of the table of dose rates. Controlling further includes determining an accumulated dosage at a sampling point, and comparing the accumulated dosage to a total desired dosage. The dose rate is adjusted based on the table of dose rate values and the determined accumulated dosage, with the dose rate ramped down as the accumulated dosage nears the total desired dosage. Accumulated dosages include fractional numbers of monitor units.

Through the present invention, a straightforward technique achieves more accurate control of radiation delivery without requiring significant and expensive hardware device changes and/or redesign. Further, a significantly higher resolution in the control of radiation delivery by the treatment system results from a reduction in dose rate that causes a corresponding reduction in the accumulated number of monitor units per sampling period. These and other advantages of the aspects of the present invention will be more fully understood in conjunction with the following detailed description and accompanying drawings.

DETAILED DESCRIPTION OF THE INVENTION

The present invention relates to modulation of radiation delivery to achieve finer resolution and control. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field of a patient, and for delimiting the field using at least one movable plate in the beam path from a radiation source. This is by way of example. Thus, the present invention is not intended to be limited to the embodiment shown but is to be accorded the widest scope consistent with the principles and features described herein.

Figure 1:
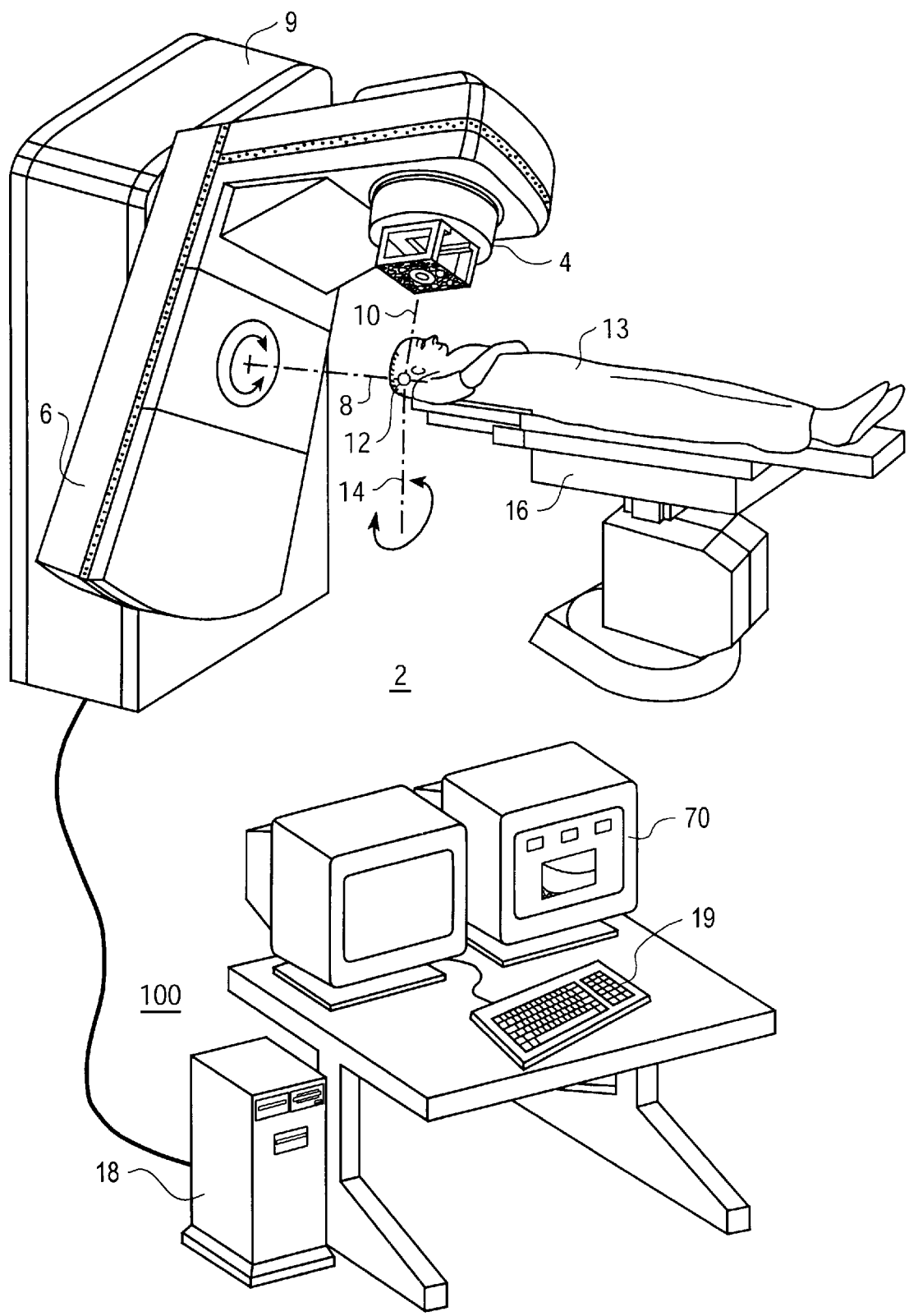
FIG. 1 illustrates a schematic diagram of a radiation treatment device including a treatment console in accordance with the present invention.

FIG. 1 illustrates a radiation emitting system 11. The radiation emitting system 11 includes a radiation treatment device 2 of common design, which utilizes plates 4 and a control unit in a housing 9 along with a treatment processing unit 100 constructed in accordance with the present invention. The radiation treatment device 2 comprises a gantry 6 which can be swiveled around a horizontal axis of rotation 8 in the course of therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated 10. Electron, photon, or any other detectable radiation can be used for the therapy.

During the treatment, the radiation beam is trained on a zone 12 of an object 13, for example, a patient who is to be treated, and who lies at the isocenter of the gantry rotation. The rotational axis 8 of the gantry 6, the rotational axis 14 of a treatment table 16, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

Figure 2:
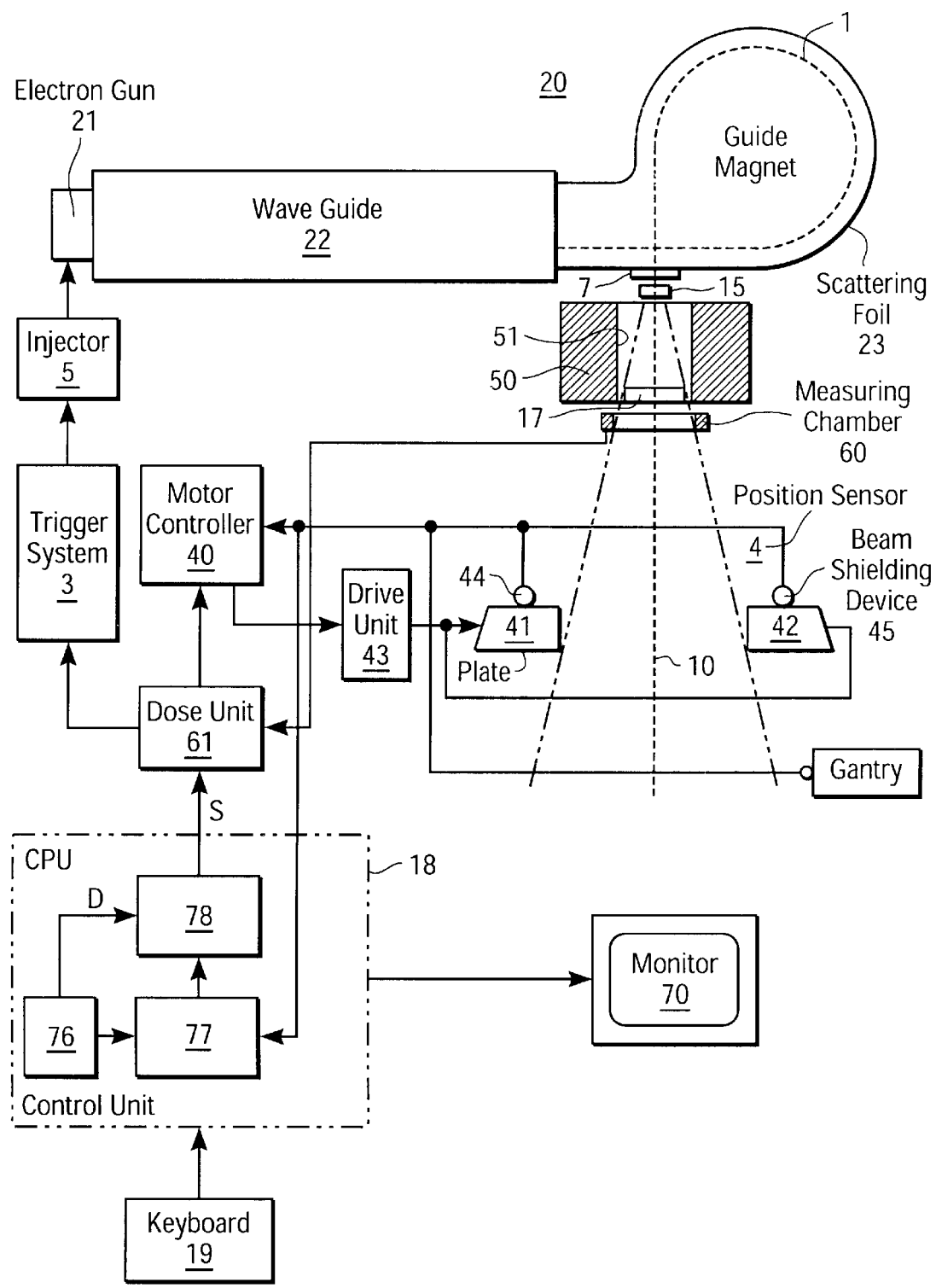
FIG. 2 is a block diagram illustrating portions of a processing unit, control unit, and a beam generation system in the radiation treatment device of FIG. 1.

FIG. 2 shows a portion of an illustrative radiation treatment device 2 and portions of treatment processing unit 100 in more detail. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, in which the dose is ascertained. If the scattering foils are replaced by a target, the radiation beam is an X-ray beam. Finally, aperture plate arrangement 4 includes a pair of plates 41 and 42. Of course, this is just one example of a beam-shielding arrangement that can be used in the invention. The invention is suitable in other arrangements, as is well appreciated by those skilled in the art.

Plate arrangement 4 comprises a pair of aperture plates 41 and 42 and an additional pair of aperture plates (not shown) arranged perpendicular to plates 41 and 42. In order to change the size of the irradiated field, the aperture plates can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions.

The area of a patient that is irradiated is known as the field. As is well known, plates 4 are substantially impervious to the emitted radiation. They are mounted between the radiation source and patient in order to delimit the field. Areas of the body, for example, healthy tissue, are therefore subjected to as little radiation as possible, and preferably to none at all. Preferably, with at least one of the plate movable, the distribution of radiation over the field need not be uniform (one region can be given a higher dose than another); further, with the gantry able to be rotated, different beam angles and radiation distributions are allowed without having to move the patient around. The central treatment processing or control unit 100 (FIG. 1) is usually located apart from radiation treatment device 2 in a different room to protect the therapist from radiation. Treatment processing unit 100 includes an output device, such as at least one visual display unit or monitor 70, and an input device, such as a keyboard 19, although data can be input also through data carriers, such as data storage devices. The treatment processing unit 100 is typically operated by the therapist who administers actual delivery of a radiation treatment as prescribed by an oncologist. By utilizing keyboard 19, or other input device, the therapist enters into a control unit 76 of the treatment processing unit 100 the data that defines the radiation to be delivered to the patient, for example, according to the prescription of the oncologist. The program can also be input via another input device, such as a data storage device, through data transmission. On the screen of a monitor 70, various data can be displayed before and during the treatment.

Central processing unit 18, included in treatment processing unit 100, is connected with the input device, e.g., keyboard 19, for inputting the prescribed delivery of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78 which suitably receives signals from the control unit 76 and memory 77 for combination to produce a set signal, S, that identifies a dose rate for dose rate control unit 61 in accordance with the present invention.

Figure 3:
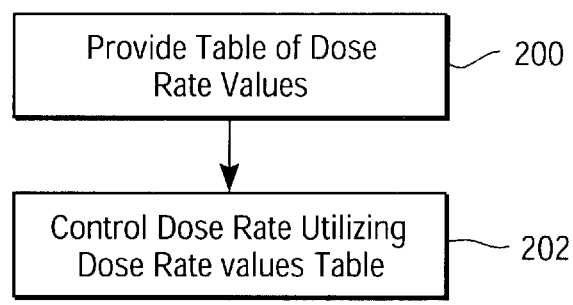
FIG. 3 illustrates a flow diagram of a process for fractional monitor unit radiation delivery in accordance with a preferred embodiment of the present invention.

FIG. 3 illustrates a flow diagram representative of a preferred method of scaling the dosage through treatment processing unit 100 in accordance with the present invention. Preferably, a table of dose rate values is provided to treatment processing unit 100 (step 200). For example, the therapist selects a desired dose rate table previously stored in memory 77 for use in a particular treatment session. The dose rate is then controlled during a treatment session through utilization of the dose rate table (step 202), e.g., via control unit 76, memory 77, combination circuit 78, and dose control unit 61. The dose rate table suitably comprises a list of dose rates, e.g., dose rate 1 to dose rate n. Each dose rate in the list has a corresponding, associated total dosage value, e.g., 39.5 MUs, 40.0 MUs, 40.1 MUs, etc. In controlling the dose rate, preferably a determination of an accumulated dose at a chosen sampling time is made. The determined accumulated dose is suitably then compared with a total dosage to be delivered for the current session. The dose rate is adjusted based on the comparison and the corresponding values in the dose rate table. The particular values in a dose rate table are dependent upon the particular needs of a treatment session, as is well appreciated by those skilled in the art.

For example, if the desired total dosage for a treatment session is a fractional number of MUs, e.g, 40.1 MUs, at each sampling point, e.g. every 10 milliseconds, during a treatment session, the total number of MUs delivered is compared with 40.1 MUs. The dose rate is then adjusted if necessary after the comparison. Preferably, as the total dosage nears the desired total dosage, the rate of delivery is modulated down. Thus, in the example, when the dosage delivered reaches 39 MUs, the rate is preferably altered according to the table values, so that, for example, at the next sampling point the total dosage is 40 MUs. The dose rate may then be adjusted even further, if desired, e.g., so that at a next sampling point, the total dosage is 40.05 MUs, and so on, until the total desired dose is delivered. The approach to the target point is therefore very fine to more accurately deliver the total desired dosage, including fractional numbers of monitor units.

Figure 4:
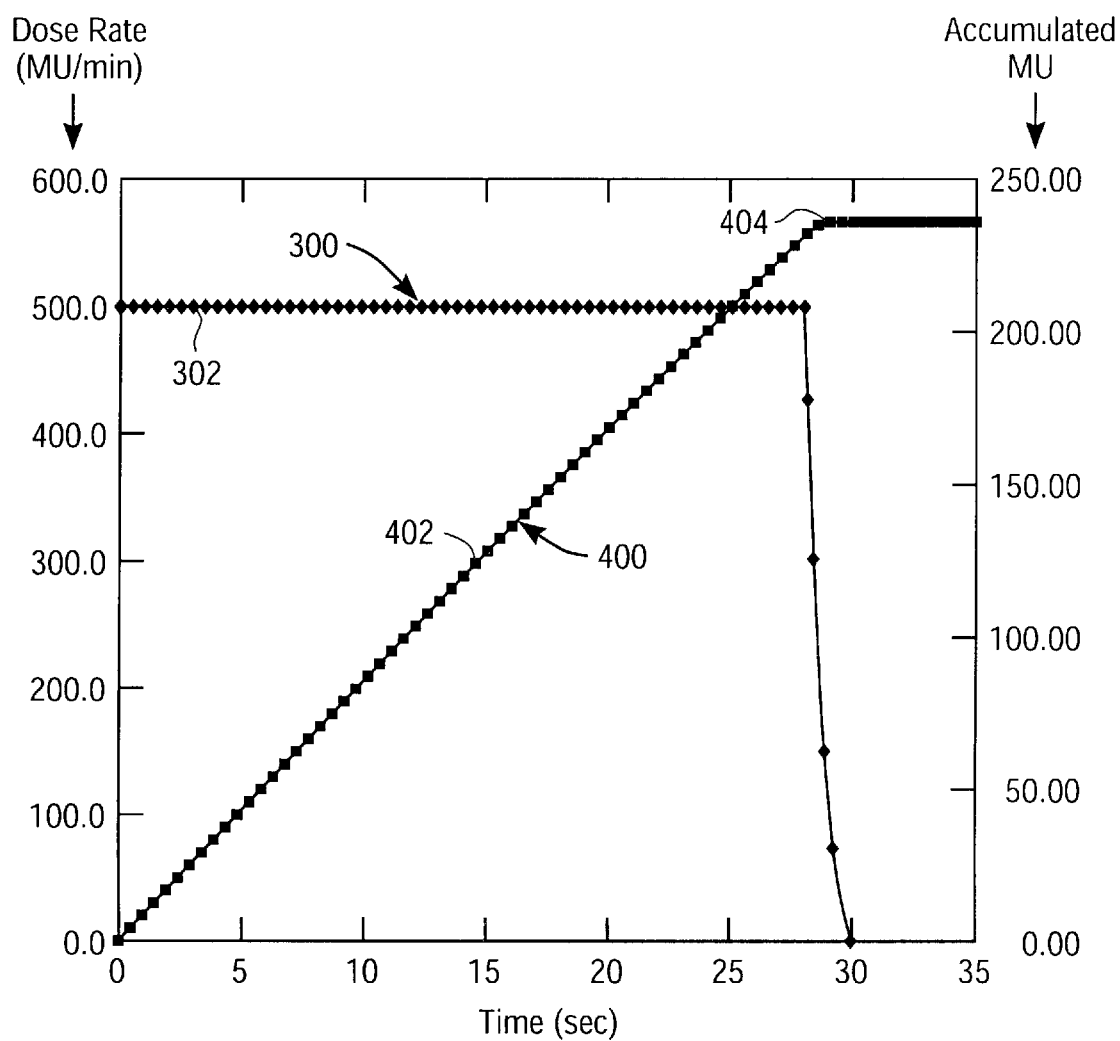
FIG. 4 illustrates a diagram of plots for an example situation contrasting the delivery of radiation in accordance with the present invention and prior art radiation delivery.

FIG. 4 illustrates a graph comparing a traditional stair step approach to dose rate (plot 300) and a modulated dose approach in accordance with the present invention (plot 400) for an example situation in which a desired total dosage delivery is 240 MUs and sampling occurs at about 0.5 second intervals. For the traditional approach, a 500 MU/min (minute) rate is utilized. At each sampling point 302, represented by diamond shapes on plot 300, the number of accumulated MUs is compared with the desired value 240 MU. Given the rate of 500 MU/min and a desired total dosage of 240 MUs, the total value should be reached in 28.8 seconds. However, if the sampling points occur every 0.5 seconds, the registered value at the 28.5 second mark remains below the desired dosage, while that at the 29 second mark would be over the desired dosage. The treatment would end, but, unfortunately, not until more radiation was delivered than actually desired.

With the present invention, however, such unfavorable extra radiation delivery is avoided. As shown by plot 400, the rate of dosage delivery is modulated over the course of the treatment session. For each sampling point 402, represented on plot 400 as squares, the desired total dosage is compared with the delivered accumulated dosage to that point. As shown, for the majority of the delivery time, the rate of dosage is fairly high and increasing fairly steadily, which aids in maintaining short treatment duration. However, at a certain sampling point, the delivered dosage is within a selected range close enough to the desired total dosage to slow the dose rate down, e.g., sampling point 404 on plot 400, as established via the dose rate table. With the dose rate slowed down, the change in accumulated dose for a next sampling point is preferably fairly close to the previous sampling point. In this manner, the desired dosage is not unduly overshot, since the decreasing of the dose rate in the final seconds of radiation delivery decreases the rate of change of the accumulated MUs, and more accurate radiation delivery, including accurate delivery of fractional numbers of MUs, is achieved.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A radiation-emitting system, comprising:

a radiation treatment device; and a treatment processing unit coupled to the radiation treatment device, the treatment processing unit controlling a dose rate of radiation emitted from the radiation emitting system by ramping down a number of monitor units per time period as an accumulated dose nears a desired total dose.

2. A radiation-emitting system according to claim 1, wherein said ramping down comprises decreasing a pulse repetition frequency.

3. A method, comprising:

providing a radiation treatment device; and providing a treatment processing unit coupled to the radiation treatment device, the treatment processing unit adapted to ramp down a number of monitor units per time period as an accumulated dose nears a desired total dose.

4. A method according to claim 3, the treatment processing unit adapted to ramp down a number of monitor units by decreasing a pulse repetition frequency.

5. A method, comprising:

determining a desired total dose of radiation; and ramping down a number of monitor units per time period as an accumulated dose nears a desired total dose.

6. A method according to claim 5, wherein said ramping down comprises decreasing a pulse repetition frequency.

7. A radiation-emitting system, comprising:

means for delivering radiation to a body; and a treatment processing unit coupled to the delivering means, the treatment processing unit adapted to ramp down a number of monitor units per time period as an accumulated dose nears a desired total dose.

8. A radiation-emitting system according to claim 7, wherein said treatment processing unit is adapted to ramp down said number by decreasing a pulse repetition frequency.

\* \* \* \* \*